United States Patent
Peng

(10) Patent No.: US 7,275,411 B2
(45) Date of Patent: Oct. 2, 2007

(54) APPARATUS AND METHOD FOR TESTING GAS DETECTION INSTRUMENTS

(75) Inventor: Wenfeng Peng, Moon Township, PA (US)

(73) Assignee: Industrial Scientific Corporation, Oakdale, PA (US)

( * ) Notice: Subject to any disclaimer, the term of this patent is extended or adjusted under 35 U.S.C. 154(b) by 167 days.

(21) Appl. No.: 10/967,270

(22) Filed: Oct. 19, 2004

(65) Prior Publication Data

US 2006/0081033 A1    Apr. 20, 2006

(51) Int. Cl.
*G01N 21/00* (2006.01)
(52) U.S. Cl. .................................... 73/1.06; 73/1.03
(58) Field of Classification Search ......... 73/1.02–1.06
See application file for complete search history.

(56) References Cited

U.S. PATENT DOCUMENTS

| | | | |
|---|---|---|---|
| 3,693,401 A * | 9/1972 | Purt et al. ................. | 73/1.05 |
| 3,997,296 A * | 12/1976 | Miller ........................... | 436/9 |
| 4,348,172 A * | 9/1982 | Miller ......................... | 431/255 |
| 6,065,779 A * | 5/2000 | Moner et al. ................. | 285/23 |
| 6,769,285 B2 * | 8/2004 | Schneider et al. .......... | 73/1.06 |
| 2001/0018844 A1 * | 9/2001 | Parekh ....................... | 73/1.06 |
| 2003/0216660 A1 * | 11/2003 | Ben-Oren et al. .......... | 600/532 |
| 2004/0074279 A1 * | 4/2004 | Forrest ....................... | 73/1.06 |
| 2006/0065303 A1 * | 3/2006 | Atkins, Sr. ................ | 137/68.11 |

* cited by examiner

*Primary Examiner*—Robert Raevis
(74) *Attorney, Agent, or Firm*—Dennison, Schultz & MacDonald

(57) ABSTRACT

An apparatus for providing a test gas to a gas monitoring instrument having a window for admitting gas to a gas sensor therein, is formed from a mechanical adaptor open at a portion thereof and having walls adapted to the gas monitoring instrument such that the mechanical adaptor removably fits over the window to form a substantially gas tight chamber of predefined volume defined by the walls of the mechanical adaptor and the instrument, means disposed in the mechanical adaptor for receiving a vial of test gas and breaking a seal in the vial to admit the test gas to the chamber. The invention is also directed to a kit including the vial of test gas, and a method for testing a gas detection instrument utilizing the apparatus and a vial of test gas.

23 Claims, 4 Drawing Sheets

APPARATUS AND METHOD FOR TESTING GAS DETECTION INSTRUMENTS

BACKGROUND OF THE INVENTION

1. Field of the Invention

The invention relates to a method and apparatus employing one or more miniature gas containers, for producing low concentration gases for testing gas detection instruments.

2. Description of Related Art

Gas detection instruments are an important category of electronic devices. They are used to safeguard human lives and property in mines, confined spaces, chemical plants and places where combustible gases ($CH_4$, etc.) or toxic gases ($CO$, $H_2S$, $SO_2$, $NO_X$, $Cl_2$, etc.) are present, or oxygen deficiency often occurs. Gas detection instruments are also widely used in domestic applications. For example, many homes have at least one detector monitoring concentrations of carbon monoxide, which is often produced by faulty furnaces or poorly ventilated fireplaces. The heart of each instrument is at least one sensor that converts chemical energy to electrical energy. The most common sensor types include metal oxide semiconductor (MOS) sensors, colorimetric sensors, thermal conductivity sensors, catalytic combustion sensors, electrochemical sensors, infrared sensors, and photo ionization and flame ionization detectors. Although most sensors possess good specificity, they are subject to changes in gas sensitivities. For example, a Galvanic type oxygen sensor can fail suddenly if the capillary hole, through which oxygen diffuses into the sensor cell, is blocked by water or liquid electrolyte. Catalytic combustion sensors that are used for detecting combustible gases can lose sensitivity completely after exposure to silicones, which form a coating on the catalyst, blocking gas reactions. The use of a defective, low sensitivity instrument is extremely dangerous as it often gives a false or misleading reading, putting human lives and property in great danger.

Gas detection instruments are required to be calibrated on a regular basis, usually monthly. Regular calibrations ensure accuracy of the instrument immediately after calibration. Since sensors can, however, fail between calibrations, users therefore need to verify the condition of their instrument prior to each use. This is a functional test done by briefly applying to the instrument a gas of known concentration and verifying instrument display and alarm operation; such a test is generally referred to as a bump test. If the instrument response is prompt and the output is within a pre-determined percentage window with reference to the test gas concentration, and the alarm devices operate as expected, the instrument is considered to be working properly. Otherwise the instrument fails the test and will need to be recalibrated and/or fully examined.

At the present time, instrument users rely on pressurized, premixed gas bottles for bump testing their instruments. A regulator is used to release the gas from the bottle and a mechanical adaptor is used to direct the gas flow to the sensor window of the instrument. Generally speaking, premixed gas bottles are large in size and inconvenient to carry in the field. The commonly used bottles are 1.2 ft³ steel and 2 ft³ aluminum with an internal gas pressure of approximately 500 psi. The gas volume is limited and the cost of each test is high. Moreover, the high pressure can cause injury if not handled properly or the bottle is exposed to excessively high temperatures.

In order to improve portability, an apparatus is available from Draeger Safety AG & Co. of Germany for conducting testing and calibration by using a 1 liter empty bottle, called a calibration bottle, and an adaptor to connect the bottle to the instrument. A gas ampoule made of glass is shattered inside the calibration bottle to allow gas to be diluted by air to a desired concentration, and the diluted gas is then introduced to the instrument through the adaptor. The apparatus has several disadvantages in that the user has to dispose broken pieces of glass every time after test and the calibration bottle is still large in size and inconvenient to carry daily in most workplaces.

Efforts have been made to generate gases onsite for testing and calibrating gas detection instruments. For example, U.S. Pat. No. 5,395,501 discloses an electrochemical generator for generating $H_2S$, $H_2$ and $Cl_2$ the generator passing an electric current through an electrolytic cell to generate the gas, which is then diluted into a carrier gas stream. U.S. Pat. No. 6,234,001 discloses an apparatus for generating a reference gas by passing a stream of carrier gas through a chamber containing a volatile liquid. As the stream passes through the chamber, the volatile liquid evaporates into a gas that blends into the carrier gas to form the reference gas.

Gas generators are available for a very limited number of gases. They are usually bulky, position sensitive, and not suitable for carrying in the field.

Due to the cost and availability, household products have been used to test equipment. Examples of this are use of gasoline vapor to test a combustible gas detector and use of cigarette smoke to test a carbon monoxide detector. Such tests are not good practice as the test gas concentrations are so high that even a badly degraded instrument may show a response, while in reality a much lower gas concentration is harmful, deadly and/or explosive.

SUMMARY OF THE INVENTION

It is therefore an object of the invention to provide a miniaturized apparatus and a method of using the apparatus for producing a gas suitable for testing gas detection instruments.

It is a further object to provide a miniaturized gas container for use with the miniaturized apparatus.

To achieve these and other objects, the invention is directed to an apparatus for providing a test gas to a gas monitoring instrument having a window for admitting gas to a gas sensor therein, comprising:

a mechanical adaptor open at a portion thereof and having walls adapted to the gas monitoring instrument such that the mechanical adaptor removably fits over the window to form a substantially gas tight chamber of predefined volume defined by the walls of the mechanical adaptor and the instrument; and means disposed in said mechanical adaptor for receiving a vial of test gas and breaking a seal in the vial to admit the test gas to the substantially gas tight chamber.

While the chamber is defined as being substantially gas tight, it is recognized that perfect gas-tightness is not necessary or easily achieved and that means must be provided for admitting gas to the chamber for test purposes. This means generally comprises a tubular needle passing through a wall of the mechanical adaptor to enable gas to flow between a gas source as will be described, and the chamber. However, the seal between the mechanical adaptor and the gas detection instrument is sufficiently gas tight that a stable test gas concentration may be maintained in the chamber for testing.

Advantageously, the apparatus of the invention may be provided in kit form including the mechanical adaptor adapted for a specific gas monitoring instrument, and one or more vials of test gas.

The invention is further directed to a method for providing a test gas to a gas detection instrument having a window for admitting gas to a gas sensor therein, comprising the steps of:

activating the gas detection instrument to determine the presence of the test gas;

mounting a mechanical adaptor open at a portion thereof and having walls adapted to the gas monitoring instrument such that the mechanical adaptor removably fits over the window to form a substantially gas tight chamber of predefined volume defined by the walls of the mechanical adaptor and the instrument, onto the instrument to form thereby said gas tight chamber containing ambient air;

mounting onto the mechanical adaptor a vial containing test gas, and breaking a seal in the vial to permit the test gas to pass into the substantially gas tight chamber;

permitting the test gas to mix with ambient air in the gas tight chamber to form a test gas mixture of known concentration; and verifying a proper response from the activated gas detection instrument.

The gas detection instrument should be activated prior to breaking the seal in the vial.

A miniature gas vial can be made of glass, plastic or metal, but is preferably made of glass due to its gas impermeability, chemical resistance and low cost characteristics. Once filled with a gas, the vial is sealed gas-tight, for example, by crimping a cap enclosure made of an aluminum seal and a PTFE/silicone septum. In the bump test, a mechanical adaptor is coupled to the instrument to be tested. The cap of the vial is then pierced by a tubular needle in the adaptor, and the gas quickly moves out of the vial to mix with the air in the chamber formed between the instrument and the adaptor to a gas concentration suitable for testing the instrument.

The concentration of the test gas can be expressed as $$C_t = C_v * V_v / (V_t + V_v) \quad (1)$$

where $C_t$ is the concentration of the test gas, $V_v$ and $C_v$ are the volume of the vial and the concentration of the gas in the vial, respectively, and $V_t$ is the volume of the dilution chamber formed by the instrument and the test adaptor. In most cases, the volume of the vial is very small when compared to the dilution chamber, thus the equation can be simplified as $$C_t = C_v * V_v / V_t \quad (2)$$

According to equation 2, a 0.3 mL, 500 ppm gas vial will make a test gas of 15 ppm when working with a test apparatus creating a volume of dilution of 10 mL.

Some instruments have more than one sensor in order to detect multiple gases. Instead of testing one gas at a time, the miniature gas vial can contain two or more gases or vapors. The balancing gas is usually air, but can be an inert gas such as nitrogen. For example, $H_2S$ is slowly oxidized by oxygen, so it is preferable to dilute $H_2S$ with nitrogen for the purpose of long term stability. Methane and other combustible gases are better diluted with nitrogen because an air mixture can be explosive when the concentration exceeds the lower explosive limit. Unlike conventional calibration and bump test methods in which a dry gas is employed, the gas in the miniature vial is diluted by ambient air so there is no significant change in the relative humidity of the environment, thus eliminating transient responses of the instrument associated with gas flow and humidity changes.

DESCRIPTION OF THE PREFERRED EMBODIMENTS

Figure 1:
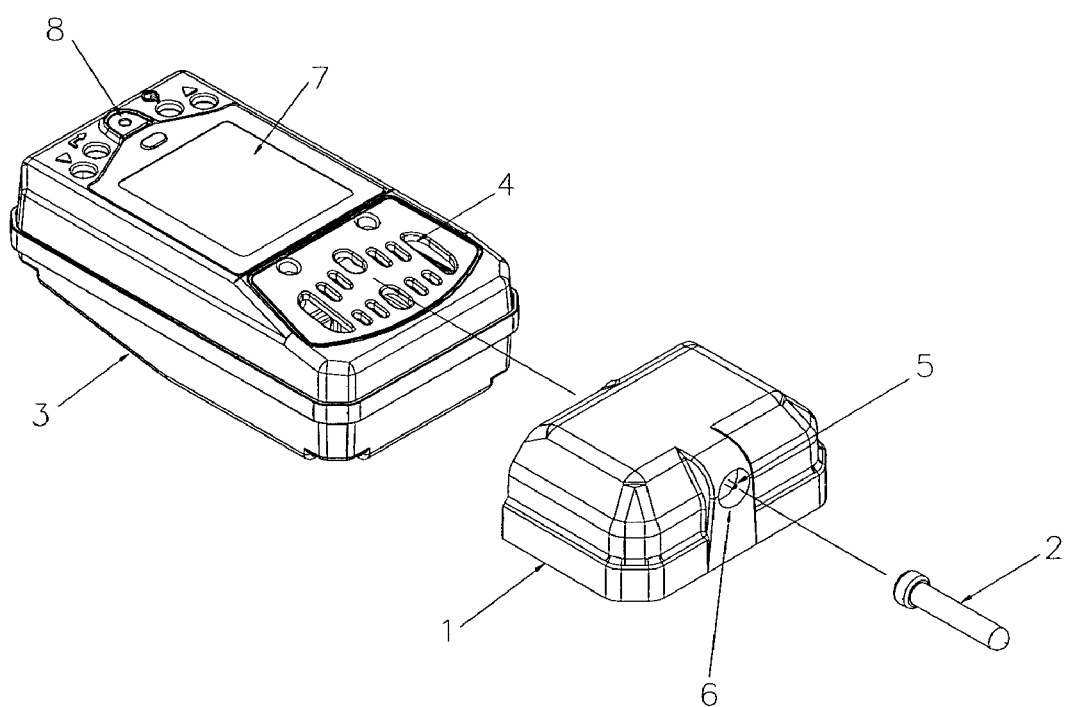
FIG. 1 is a perspective exploded view of a test apparatus according to a preferred embodiment of the invention.
Figure 2:
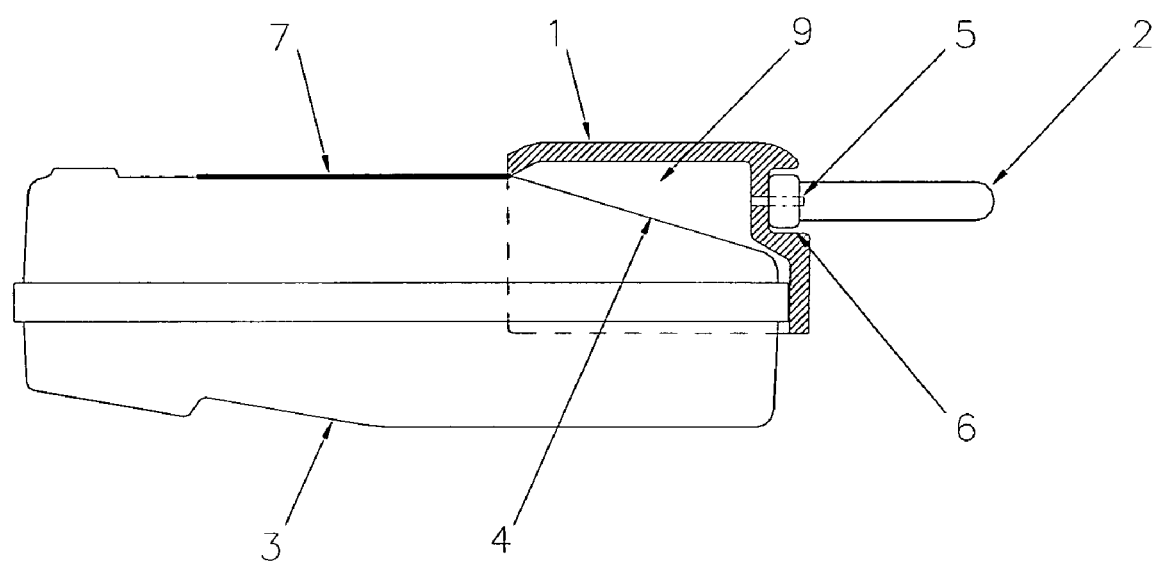
FIG. 2 is a side view in partial cross-section of a test apparatus according to the invention mounted on a gas sensor.

An apparatus in accordance to the invention is illustrated in FIGS. 1 and 2, including a mechanical adaptor 1 and a miniature gas vial 2. The adaptor 1 is adapted to mount on a gas monitoring instrument 3 which includes a window 4 for admission of gas to sensors which are partially shown behind the windows. The adaptor 1 has a shape similar to that of a calibration cup, which is used by most gas monitoring instruments to direct a test gas to the instrument for calibration. The adaptor 1 further comprises a tubular needle 5 disposed in a recess 6 for protecting the needle 5 and the user.

This sensor window 4 of the instrument 3 comprises of one or more openings in the instrument housing adjacent the sensors inside the instrument. The window 4 exposes the sensor to gases in the surrounding atmosphere. Normally the sensor window is covered with a porous polymer material such as a PTFE membrane to protect the sensor and electronic components from contamination by dust and moisture.

In the test mode shown in FIG. 2, the mechanical adaptor 1 is coupled with the instrument 3 in a manner generally known in the art to completely cover the sensor window so that the headspace of the sensor is isolated from the surrounding atmosphere. A gas-tight chamber 9 of known volume is thus formed between the instrument faceplate and the inner wall of the adaptor 1, the chamber 9 containing ambient air. The volume of chamber 9 determines the concentration of the test gas; the smaller the volume, the higher the concentration of the test gas, and therefore, a higher response should be expected from the instrument. The adaptor 1 should not cover the LCD display 7 and LED visual alarm indicators 8 on the instrument face.

The tubular needle 5 in the adaptor 1 is preferably made of stainless steel due to its strength and corrosion resistance. The length and inner diameter of the needle will FINN generally be in the range of 2-10 mm and 0.5 to 1.5 mm, respectively. The needle has an outer diameter suitable for penetrating the cap of the vial. However, if the inner diameter of the needle is too small, or if the needle is too long, it will take a long time for the gas to diffuse and mix with the air in the dilution chamber, causing a long response time of the instrument.

A suitable needle is Model 18 GP dispensing tip manufactured by EFD Inc, RI, USA. The stainless steel needle has a blunt tip and an inner diameter of approximately 0.85 mm.

In a bump test, the vial is pushed by force against the metal needle until the needle penetrates the cap closure, in the manner shown in FIG. 2. Gas in the vial quickly diffuses through the needle to form a homogeneous gas mixture in the chamber between the adaptor 1 and the faceplate of the instrument 3. The sensors in the instrument are subsequently exposed to the gas in the chamber, and a working instrument should respond to the gas quickly and change its gas reading if the instrument has a readout display. If the concentration reaches a preset threshold value, a visual and audible alarm should be activated. The test adaptor is removed from the instrument when the test is completed.

Although most sensors respond to gas very quickly, some sensors require 30 seconds or more to establish a stable signal.

The end of the vial with the piercable seal preferably fits sealingly in the recess formed in the mechanical adaptor 1, such that the mechanical adaptor 1, the vial 2 and the monitoring instrument 3 form a gas tight space. Any gas leakage is thereby minimized and the concentration of the test gas remains relatively stable during the test. A failure of this gas tight space will allow gas to leak out of the chamber, causing a low and unstable concentration of the test gas, and affect the instrument responses.

Miniature vials containing gas are known for use in gas chromatography, and are available in different forms and shapes from Kimble Glass, Inc., Agilent Technologies and other manufacturers. These vials usually have a body made of glass, metal or plastic materials with a water capacity of 0.1 to 2.0 ml. Glass is preferred because it is impermeable to gas, inert to most reactive gases and has low gas adsorption coefficients, properties which enable a long shelf life for the gas contained in the vials.

The pierceable seal generally comprises a septum made of one or two polymeric elastomers of low gas permeability. Typical septum materials include silicone, butyl, Viton® (a fluorocarbon), polytetrafluoroethylene (PTFE), Nitrile (Buna-N), Neoprene, and urethane. The most used septa are silicone, PTFE/silicone (with PTFE facing the gas), and PTFE/silicone/PTFE.

Figure 3:
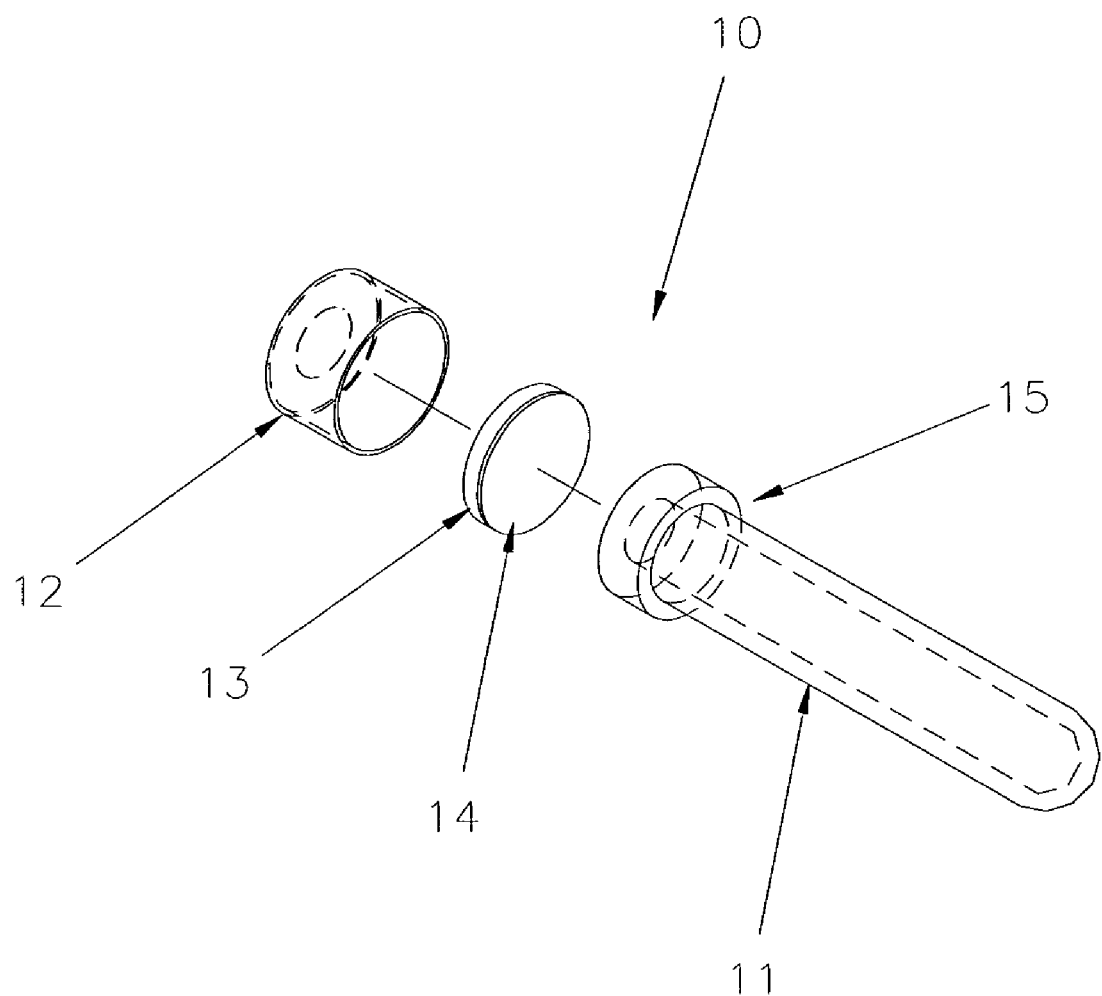
FIG. 3 is a perspective exploded view in partial cross-section of a miniature gas vial suitable for use according to the present invention.

A minivial suitable for this application is shown in FIG. 3. Vial 10 has a glass body 11 made of borosilicate glass, an aluminum cap 12 with an opening in the center, and a septum comprising a silicone layer 13 and a PTFE resin layer 14. The PTFE layer 14, which is exposed to the gas in the vial, is laminated to the silicone layer 13 to protect the silicone layer from exposure to gases in the vial, since gases such as $H_2S$ and $Cl_2$ are reactive and may cause the silicone to degrade. The glass body 11 further comprises a neck 15 to enable crimping the cap assembly to the glass body 11 to achieve a gas tight closure.

Miniature gas vials can be made by sealing open vials in an atmosphere having a gas of a fixed concentration, e.g. 1.0% CO, through an automated assembly process to achieve consistency. The pressure of gas inside the tube can be maintained at approximately 1 atm if 1 atm pressure is maintained in the filling environment. A gas vial can also be filled with two or more gases for use in bump testing instruments having sensors for detecting multiple gases simultaneously. For easy identification of gases in the vials, the tops can be color coded.

Figure 4:
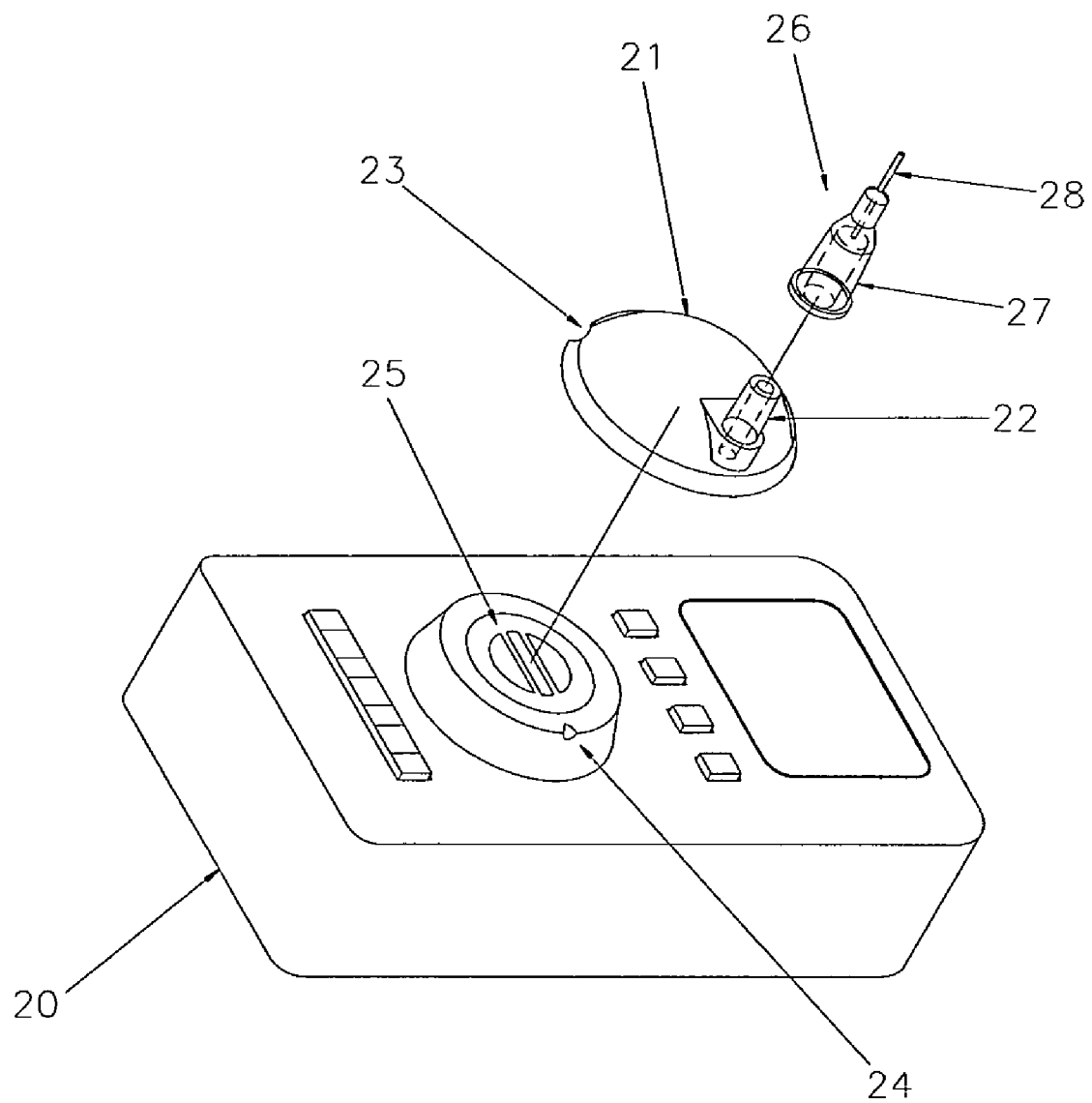
FIG. 4 is a perspective exploded view of a test apparatus according to a further embodiment of the invention.

FIG. 4 shows a mechanical adaptor that can be used both for bump testing and instrument calibration. The mechanical adaptor 21 is used with a gas detection instrument 20 in which the sensor window is part of a raised portion 25. Adaptor 21, in a generally cup shape, fits over the raised portion 25 to form a substantially gas tight chamber, and the adaptor 21 has a male Luer fitting passing through its wall to admit gas to the chamber. A corresponding female Luer fitting 26 includes a plastic hub 27 and a tubular stainless steel needle 28.

The adaptor 21 is formed with a notch 23, and the raised portion 25 is formed with a corresponding notch 24. When the adaptor 21 is used for bump testing, the adaptor is mounted with the notch 23 not aligned with the notch 24, forming a substantially gas tight chamber. The female Luer fitting 27 is fitted tightly onto the male Luer fitting 22, and needle 28, which is an integral part of the female Luer fitting 27, is used to puncture the septum on a vial as previously described, allowing gas to escape from the vial into the substantially gas tight chamber.

When the adaptor is used for calibration, the notches 23 and 24 are aligned so that gas can escape from the chamber. A higher pressure source of gas of known concentration, such as a gas cylinder, is used, connected to the male Luer fitting with standard polymeric tubing. A stream of gas is applied to the instrument, which escape through the aligned notches.

The apparatus and method described can be used for testing instruments employing various sensor technologies. The apparatus has greater portability than the existing methods, which require the use of at least one bottle of compressed gas. Such compressed gas bottles need to be stored in large carrying cases, and may explode when exposed to high temperatures. By contrast, an apparatus according to the invention can be as small as a match box with a gas vial smaller than half the size of a finger tip. It is light in weight and is safe to use. Because of this small volume, the gas in a miniature vial will not affect human health if it accidentally leaks out. Moreover, in the case of accidental leakage from the vial, the instrument being tested will show a low or no response to the vial, resulting in further investigation of the instrument, but the user will not be led to believe that the instrument is working properly.

The use of the apparatus and method according the present invention should significantly reduce the cost of gas tests. Only one miniature vial is needed for a bump test and the cost per vial is lower than $0.25, which is a small fraction of the cost of conventional methods.

EXAMPLE

A Model STX-70 carbon monoxide detector manufactured by Industrial Scientific Corporation, Oakdale, Pa., is tested by a test kit and method according to the invention. The instrument includes a sensor window in the top of the instrument case and a LCD screen in the front for displaying gas concentration. The lower level alarm threshold is set at 35 ppm.

The test kit includes a test adaptor and miniature test gas vials of 0.3 mL water capacity. The adaptor has a cup shape with a recess in the outside wall, in which a tubular stainless steel needle type 18 GP (EFD Inc, USA) is located. The needle has an inner diameter of 0.85 mm, and a length of 4 mm. When the adaptor is coupled with the instrument, a chamber of approximately 3.5 mL is formed between the instrument and the inner wall of the adaptor. The vials, supplied by Sun Sri, USA, are filled in a glove box with 997 ppm CO in air at 1 atm pressure, and are sealed with a crimp top formed of an aluminum overcap and a silicone septum.

When the septum is punctured with the needle, the CO concentration in the chamber should rise to 79 ppm (calculated from equation 1, above). The pass/fail limit is set at 30% error from the calculated value so the minimum required gas reading is 55 ppm.

In conducting the bump test, the instrument was turned on and zeroed in a clean atmosphere. The test adaptor is mounted securely to the instrument, and a minivial is held with the cap facing the adaptor and then pushed against the needle unitl a snap sound is heard (i.e. the cap is pierced). The instrument reading changes quickly, and within 15 seconds the visual and audible alarms are activated. At 25 seconds the instrument reading reaches 62 ppm. Since this reading exceeds the minimum requirement, the instrument passed the test. The adaptor is removed from the instrument to complete the test.

What is claimed is:

1. An apparatus for providing a test gas to a gas monitoring instrument, which instrument includes a rigid housing that contains at least one gas sensor, and which includes in an exterior face of the rigid housing an aperture therethrough providing a window for admitting gas through the aperture and to the at least one gas sensor therein, comprising:
    a generally cup shaped mechanical adaptor open at a portion thereof and having walls surrounding the open portion which are adapted to the gas monitoring instrument such that the mechanical adaptor removably fits over the window with the open portion disposed over the window to form a substantially gas tight chamber of predefined volume defined by the walls of the mechanical adaptor and the face of the instrument; and
    means disposed in said mechanical adaptor for receiving a miniature vial of test gas externally to said substantially gas tight chamber with the mechanical adaptor in place, and means for breaking a seal in the vial to admit the test gas to the substantially gas tight chamber.

2. The apparatus according to claim 1, wherein the receiving means is a recess in an outer wall of the mechanical adaptor.

3. The apparatus according to claim 1, wherein the breaking means comprises a tubular needle for passing test gas between the vial and the chamber.

4. The apparatus according to claim 3, wherein the needle comprises stainless steel.

5. The apparatus according to claim 4, wherein the needle has an inner diameter of 0.1-2 mm.

6. The apparatus according to claim 1, additionally comprising a vial of test gas received in the receiving means.

7. The apparatus according to claim 6, wherein the vial comprises a glass container having a mouth closed by a pierceable seal.

8. The apparatus according to claim 7, wherein the piercable seal comprises a layer of polytetrafluoroethylene polymer disposed facing said container and a layer of silicone disposed facing away from said container.

9. The apparatus according to claim 8, wherein the vial further comprises an aluminum overcap with an opening therein crimped to a neck of said container, the piercable seal being held in place between the overcap and the mouth of the container.

10. The apparatus according to claim 9, wherein the receiving means is a recess in an outer wall of the mechanical adaptor, the breaking means comprises a tubular needle for passing test gas between the vial and the chamber and the overcap is constructed and arranged to fit within the recess with the tubular needle piercing the piercable seal.

11. The apparatus according to claim 1, wherein the receiving means comprises a male Luer fitting.

12. The apparatus according to claim 11, additionally comprising a female Luer fitting including a tubular needle, and a vial of test gas with a pierceable seal, the female Luer fitting being disposed between the male Luer fitting and the vial, with the needle puncturing the pierceable seal.

13. The apparatus according to claim 1, wherein the mechanical adaptor comprises means for selectively releasing gas from the substantially gas tight chamber.

14. A kit for providing a test gas to a gas monitoring instrument, which instrument includes a rigid housing that contains at least one gas sensor, and which includes in an exterior face of the rigid housing an aperture therethrough providing a window for admitting gas through the aperture and to the at least one gas sensor therein, comprising:
    a generally cup shaped mechanical adaptor open at a portion thereof and having walls surrounding the open portion which are adapted to the gas monitoring instrument such that the mechanical adaptor removably fits over the window with the open portion disposed over the window to form a substantially gas tight chamber of predefined volume defined by the walls of the mechanical adaptor and the face of the instrument;
    means disposed in said mechanical adaptor for receiving a miniature vial of test gas externally to said substantially gas tight chamber with the mechanical adaptor in place, and means for breaking a seal in the vial to admit the test gas to the substantially gas tight chamber, and
    a miniature vial of test gas constructed and arranged to be received in the receiving means and comprising a seal which is breakable when the vial is received in the receiving means.

15. The kit according to claim 14, wherein the receiving means is a recess in an outer wall of the mechanical adaptor.

16. The kit according to claim 14, wherein the breaking means comprises a tubular needle for passing test gas between the vial and the chamber.

17. The kit according to claim 16, wherein the needle is a stainless steel needle.

18. The kit according to claim 14, wherein the vial comprises a glass container having a mouth closed by a pierceable seal.

19. The kit according to claim 18, wherein the pierceable seal comprises a layer of polytetrafluoroethylene polymer disposed facing said container and a layer of silicone disposed facing away from said container.

20. The kit according to claim 18, wherein the vial further comprises an aluminum overcap with an opening therein crimped to a neck of said container, the pierceable seal being held in place between the overcap and the mouth of the container.

21. The kit according to claim 20, wherein the receiving means is a recess in an outer wall of the mechanical adaptor, the breaking means comprises a tubular needle for passing test gas between the vial and the chamber and the overcap is constructed and arranged to fit in the recess with the tubular needle piercing the piercable seal.

22. A method for providing a test gas to a gas detection instrument, which instrument includes a rigid housing that contains at least one gas sensor, and which includes in an exterior face of the rigid housing an aperture therethrough providing a window for admitting gas through the aperture and to the at least one gas sensor therein, comprising the steps of:
    activating the gas detection instrument to determine the presence of the gas;
    mounting a generally cup shaped mechanical adaptor open at a portion thereof and having walls surrounding the open portion which are adapted to the gas detection instrument such that the mechanical adaptor removably fits over the window with the open portion disposed over the window to form a substantially gas tight chamber of predefined volume defined by the walls of the mechanical adaptor and the face of the instrument, onto the instrument to form thereby said substantially gas tight chamber containing ambient air;

externally mounting onto the mechanical adaptor a miniature vial containing test gas, and breaking a seal in the vial to permit the test gas to pass into the gas tight chamber, wherein the vial comprises a glass container and a pierceable seal, and wherein said mounting the vial comprises piercing the seal with a tubular needle to admit the test gas to the substantially gas tight chamber;

permitting the test gas to mix with ambient air in the substantially gas tight chamber to form a test gas mixture of known concentration; and verifying a proper response from the activated gas detection instrument.

23. The method according to claim 22, wherein the tubular needle comprises stainless steel and has an inner diameter of 0.1-2 mm.

* * * * *